(12) United States Patent
Thompson

(10) Patent No.: US 8,932,218 B1
(45) Date of Patent: Jan. 13, 2015

(54) METHODOLOGY, USE AND BENEFITS OF NEUROACOUSTIC FREQUENCIES FOR ASSESSING AND IMPROVING THE HEALTH AND WELL-BEING OF LIVING ORGANISMS

(76) Inventor: Jeffrey D. Thompson, Carlsbad, CA (US)

( * ) Notice: Subject to any disclaimer, the term of this patent is extended or adjusted under 35 U.S.C. 154(b) by 0 days.

(21) Appl. No.: 12/709,249

(22) Filed: Feb. 19, 2010

Related U.S. Application Data

(60) Provisional application No. 61/153,753, filed on Feb. 19, 2009, provisional application No. 61/153,675, filed on Feb. 19, 2009.

(51) Int. Cl.
*A61B 5/00* (2006.01)
*A61B 5/024* (2006.01)

(52) U.S. Cl.
CPC ............. *A61B 5/742* (2013.01); *A61B 5/02405* (2013.01)
USPC ............................ 600/301; 600/300; 600/509

(58) Field of Classification Search
CPC ... A61B 5/742; A61B 5/02405; A61B 5/7405
USPC .......................................... 600/509, 300, 301
See application file for complete search history.

(56) References Cited

U.S. PATENT DOCUMENTS

| | | | |
|---|---|---|---|
| 6,656,137 B1 * | 12/2003 | Tyldsley et al. | 601/15 |
| 2004/0230252 A1 * | 11/2004 | Kullok et al. | 607/48 |
| 2006/0030907 A1 * | 2/2006 | McNew | 607/88 |

* cited by examiner

*Primary Examiner* — Christopher D Koharski
*Assistant Examiner* — Philip Edwards
(74) *Attorney, Agent, or Firm* — The Maxham Firm

(57) ABSTRACT

The ANS of a subject is continuously monitored to obtain the sympathetic nervous system (SNS) and parasympathetic nervous system (PSNS) components of the autonomous nervous system while an external stimulus is applied to the subject having a frequency that sweeps across a frequency band. The stimulus may be a vibration, flickering light or sound. The ANS is determined to have entered into a state of homeostasis when the SNS component equals the PSNS component. The value of frequency that corresponds to the state of homeostasis is selected as the fundamental frequency of the subject for use in subsequent treatment protocols.

12 Claims, 7 Drawing Sheets

METHODOLOGY, USE AND BENEFITS OF NEUROACOUSTIC FREQUENCIES FOR ASSESSING AND IMPROVING THE HEALTH AND WELL-BEING OF LIVING ORGANISMS

CROSS-REFERENCE TO RELATED APPLICATIONS

This application claims the benefit of U.S. Provisional Application 61/153,753 filed on Feb. 19, 2009, and U.S. Provisional Application 61/153,675 filed on Feb. 19, 2009. The teachings of both of these applications are incorporated herein by reference.

FIELD OF THE INVENTION

This invention relates generally to treating a patient with specifically tuned sonic, optical or vibrational energy to affect the patient's mental, emotional or physiological state, using manual, semi-automated or fully automated systems, or any combination thereof, for encouraging desirable mental, emotional and physical conditions.

BACKGROUND OF THE INVENTION

The autonomic nervous system (ANS), of which the brain is a part, is that portion of the nervous system of humans and that of many other animals which controls the functioning of glands, organs, and "involuntary" muscle motions, for example, heart muscles, smooth muscles that constrict or relax blood vessels, the stomach, etc. The autonomic nervous system has two branches referred to as the sympathetic nervous system (SNS) and the parasympathetic nervous system (PSNS).

The SNS controls responses that help the body cope with challenges. For example, when the SNS is stimulated by the challenge of driving down a freeway onramp, it releases neurotransmitters that result in an increase in heart rate and blood pressure, dilation of the pupils, reduction of digestive activities, and other related responses.

The PSNS releases neurotransmitters that cause a balancing between the SNS and the PSNS, an increase or decrease of activities as needed for health, for example, digestive activities, blood sugar, immune responses, and other like responses. Such responses are associated with relaxation and absence of internal or external threatening or stressful stimuli.

Many of the stimuli that challenge the nervous system are seen as unpleasant but relatively unavoidable parts of modern life. These include, for example, job pressures, driving in heavy traffic, noisy neighbors, etc. Other stimuli are sought after, such as those produced by exciting movies, sports, music and other sounds or events which can cause stress in the ANS by over-arousal, fear, anxiety, bewilderment, or any one of a number of other emotions.

Unfortunately, the average person is often so inundated by stressful and/or demanding stimulation that relaxation itself is an effort or unattainable. Stress is acknowledged as the "Silent Killer" and seen as the causality of many diseases. Stress also often leaves an individual unable to cope and react in a calm manner, unable to think clearly and to otherwise respond to stress in socially acceptable ways. Relaxation is now seen as a health treatment that must be taken periodically, often with the aid of additional stimuli which have the effect of reducing stress, such as certain nutraceuticals, relaxing fragrances, music, sounds, massages, activities, events and/or combinations thereof.

In actuality, stimulation and relaxation are vital components in keeping the body and mind functioning properly. Neither state is inherently superior or healthier. Functionality and health are optimized when the SNS and PSNS are dynamically and interactively in a state of balance much of the time. This balanced state is called "homeostasis."

Chronically over-stimulated humans and animals frequently lose the ability to return naturally to a state of equilibrium or homeostasis. Part of the challenge is that homeostasis, as such, does not have physical signs obvious to most adults and is not cognized by animals, children and impaired individuals. Thus, a person cannot use physical cues to alert or train himself or herself into the state of homeostasis and a balanced state of the ANS.

There is, therefore, a need for a systematic method for inducing homeostasis in a patient (human or otherwise) that does not rely upon the subjective determinations of that patient.

SUMMARY OF THE INVENTION

In one aspect a method for determining a fundamental frequency of the autonomic nervous system (ANS) of a subject is disclosed. In various embodiments the ANS of the subject is monitored to obtain a sympathetic nervous system (SNS) component of the ANS and a parasympathetic nervous system (PSNS) component of the ANS. At least an external stimulus is applied to the subject, the external stimulus having at least a first frequency. By way of example, the external stimulus may be one or more of vibration at the first frequency, light flickering at the first frequency or sound with a tone at the first frequency. The first frequency is changed and the SNS component and the PSNS component are continuously monitored to determine when the ANS has entered into a state of homeostasis. In preferred embodiments, determining when the ANS has entered into a state of homeostasis includes determining if the SNS component and the PSNS component are substantially equal. The value of first frequency that corresponds to the state of homeostasis is then determined, which in preferred embodiments comprises determining the value of the first frequency when the SNS component and the PSNS component are substantially equal. Then, the fundamental frequency is selected as this determined value of the first frequency. In preferred embodiments, a frequency sweep is performed with a predetermined frequency band based upon the subject. In certain embodiments, both a first and a second frequency are supplied to the subject, in which the second frequency is an octave of the first frequency.

In another aspect a system for determining a fundamental frequency of a subject is disclosed. The system includes a monitor for monitoring the ANS of the subject to obtain the SNS and PSNS components of the ANS, a frequency application device for applying at least an external stimulus to the subject according to an input signal; and a computing system coupled to the monitor and to the frequency application device. The computing system is programmed to generate a signal having a first frequency and to output the signal to the frequency application device; change the first frequency; monitor the SNS component and the PSNS component to determine when the ANS has entered into a state of homeostasis; determine a value of the first frequency that corresponds to the state of homeostasis, and select as the fundamental frequency the determined value of the first frequency. In various embodiments the frequency application device may be one or more of a surface that vibrates at a frequency according to the input signal, a light that flickers according to the input signal and sound system that plays a tone according to the input signal. In preferred embodiments the monitor is a Real-Time Heart Rate Variability monitor.

DETAILED DESCRIPTION

A method and related system for accurately and objectively determining when a subject is in homeostasis and for placing the subject into homeostasis are generally described herein. Related treatment methods are also disclosed.

By way of example with a preferred embodiment, the components of the ANS of a subject, and the state of homeostasis thereby, can be detected with a particular type of cardiac monitor, called a Real-Time Heart Rate Variability (RT-HRV) monitor. RT-HRV monitors are well known in the medical arena, and any suitable device may be employed. It will be appreciated that other devices or monitors, however, may also be suitably employed that are capable of obtaining SNS and PSNS data in real-time to advance the embodiment methods as described in the following, such as EEG devices or the like. It will be further appreciated that such real-time data collection devices may require an initial data-gathering period before they begin outputting SNS and PSNS data, and that once they begin producing data they may introduce a time lag, such as one second or less, between the occurrence of an event and when such event is indicated in the SNS and PSNS data. So long as such delays are not sufficiently significant to introduce errors in the following methods the data collection may be considered in "real-time." It will be further appreciate that aspects of such a monitor may be contained within a computer system as described below, such that the computing system obtains raw data from an interface that is then processed into the SNS and PSNS components. Alternatively, the computer system may accept SNS and PSNS components directly from the interface itself.

Figure 1:
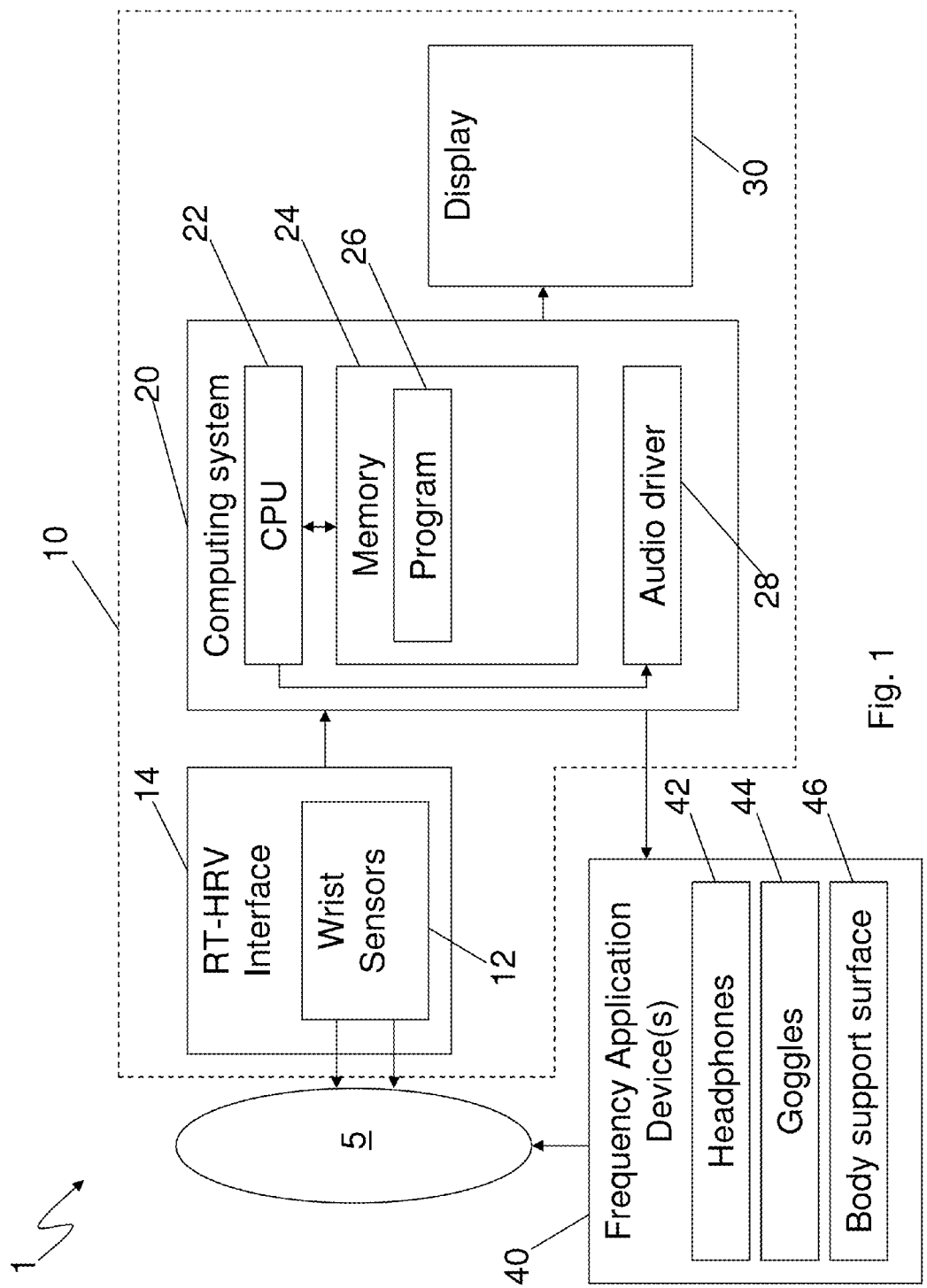
FIG. 1 is a block diagram of an embodiment of the system.

As illustrated in FIG. 1, an embodiment RT-HRV 10 may include, for example, two wrist sensors 12 that may be attached to the wrists of a user 5 with cloth elastic bands, as known in the art. These sensors 12 detect the heart rate of the subject and connect to an interface 14. As known in the art, the interface 14 processes the signal data received from the sensors 12 to generate corresponding heart rate data. The interface 14, in turn, may connect to a computer system 20, such as through a USB interface, to provide the heart rate data to the computer 20. The computer 20 includes a central processing unit (CPU) 22 coupled to memory 24, as known in the art. The memory 24 includes a computer program 26 executable by the CPU 22 to perform various steps that processes the heart rate data, as discussed in the following. Any suitable method may be employed to create the computer program 26, which should be well within the skill of one of ordinary skill after reading the following. It will be further appreciated that in the methods enumerated below, the computer system 20 may include one or more CPUs 22 with corresponding memory 24, with each CPU 22/memory 24 configuration potentially handling a separate task, steps or sub-routines to practice the embodiment methods. For example, one CPU 22 and memory 24 sub-system may be dedicated solely to generating SNS and PSNS data and being physically located within the interface 14, submitting the SNS and PSNS data to another CPU 22 and memory 24 sub-system that processes such data to perform the bio-feedback and monitoring methods discussed in the following while providing corresponding output on the display 30. Other variations are certainly possible, and such variations and multi-processor computing systems, or networked computing systems, are well-known in the art and may be successfully employed in the following; for ease of description all of these variations are generally lumped together and broadly referenced as the computing system 20. More generally still it will be appreciated that many of the components of not only the computer system 20 but of the other components in the system 1 may be networked together over a local area network, wide area network or both. For example, the ANS monitoring component 14 may be remotely positioned together with the subject 5 and one or more frequency application devices 40, which are all coupled to the computer system 20 via, for example, a wide area network or a local area network.

Heart rate variability is the measure of variations in the time between beats of the heart of the subject. Electrical signals over a range of frequencies cause the portions of the heart to contract or relax in the proper sequence to create a beat, or pumping cycle. Preferred embodiments of the program 26 may employ conventional spectral analysis of the heart data as provided by the RT-HRV interface 14, as known in the art, to show SNS and PSNS activity. Preferred embodiments of the program 26 generate HRV data that is conformal to known standardizations, such as the European taskforce of Cardiology, the American Heart Association and the American Association of Cardiology and Pacing. The program 26 may cause the CPU 22 to process the HRV data, decompose it into its SNS and PSNS components in accordance with known techniques and standards, and then present this data in various formats upon a display 30 coupled to the computing system 20, as known in the field. Various embodiment methods and related systems then employ this conventional SNS and PSNS data to gradually re-train the ANS to function in a state of equilibrium or balance, as discussed in the following.

Figure 2:
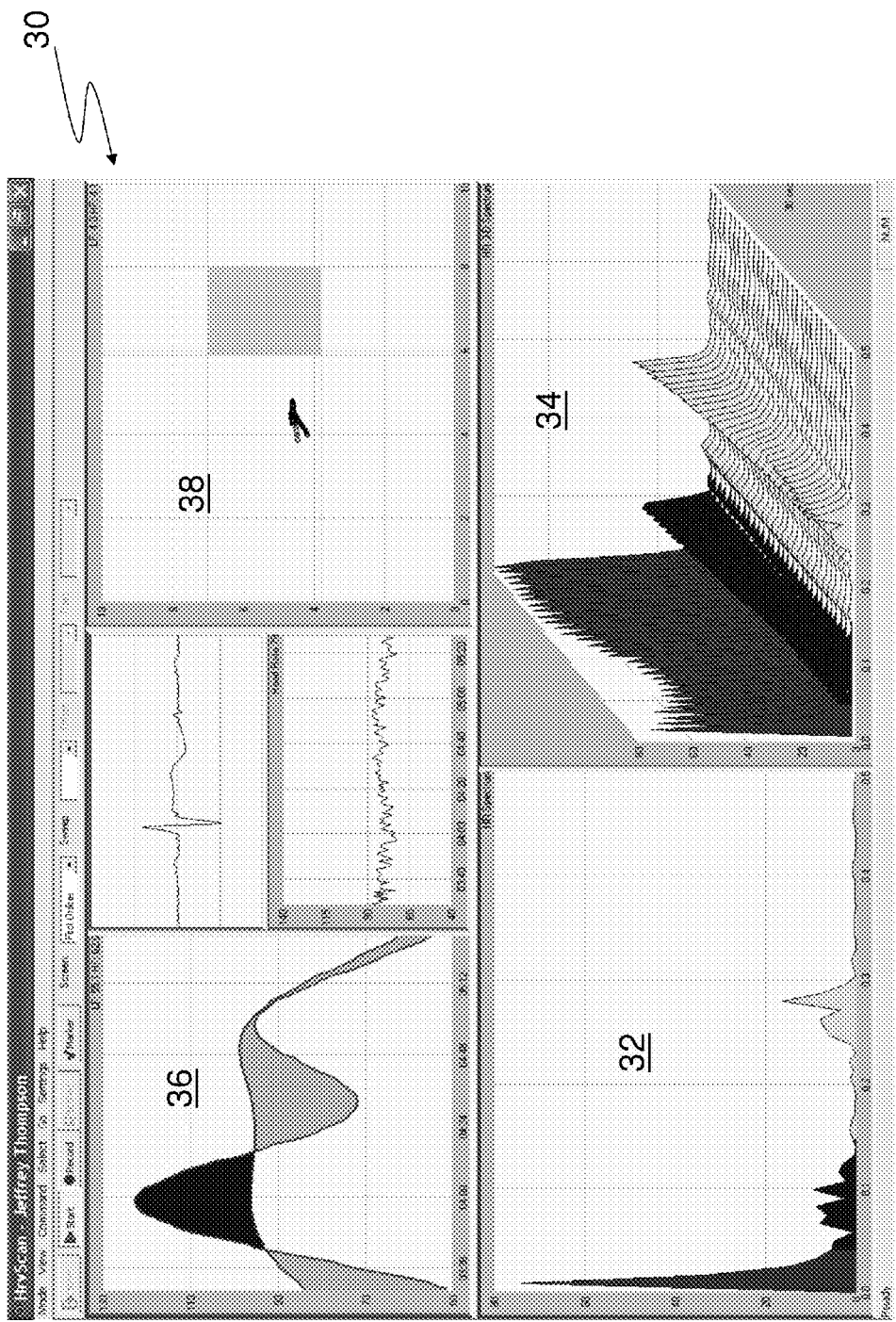
FIG. 2 is a screen shot of an embodiment display.
Figure 6:
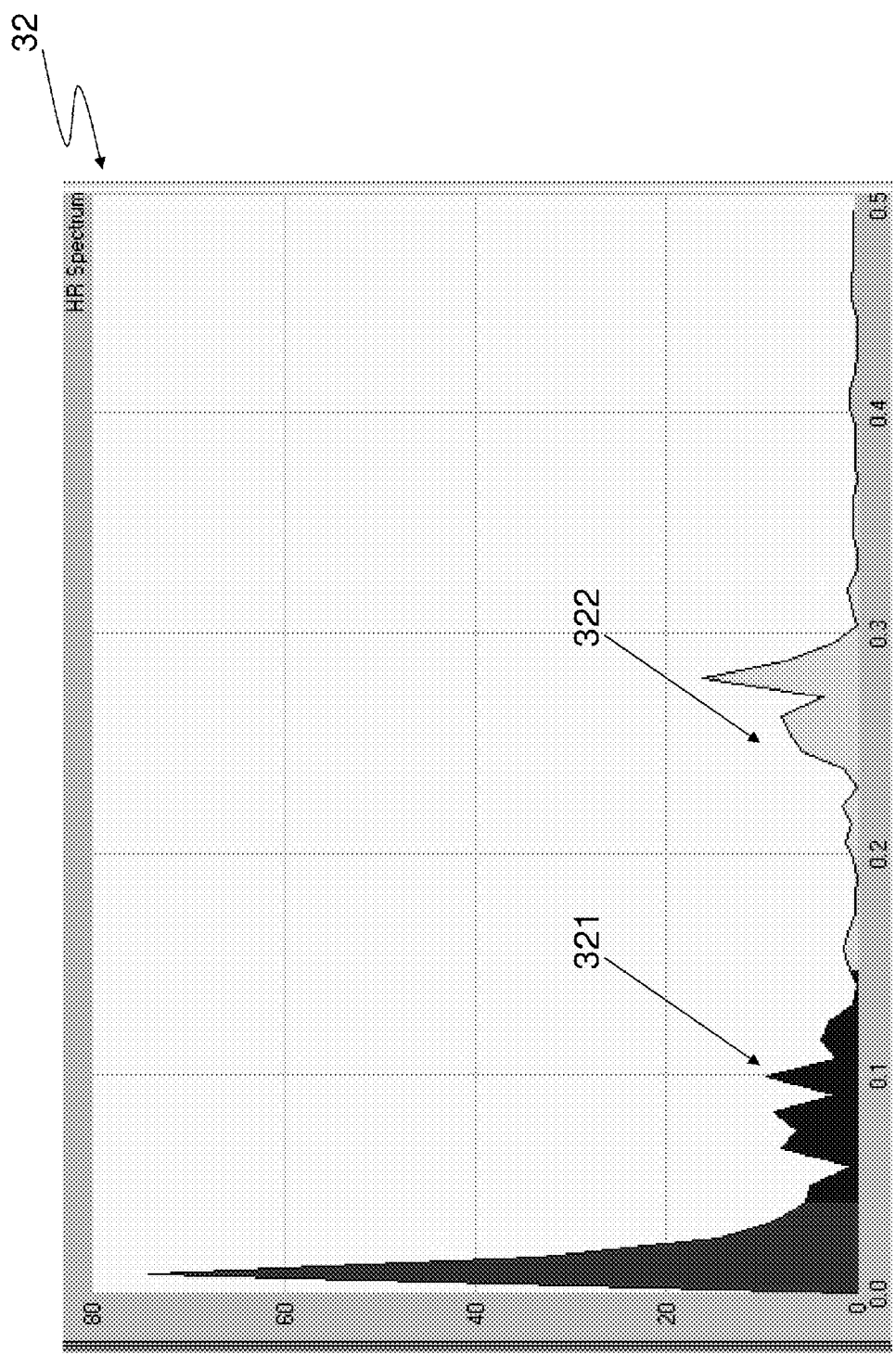
FIG. 6 is a detailed view of a window in the embodiment display shown in FIG. 2 showing heart rate spectrum data.

FIG. 2 illustrates embodiment output shown on display 30 for the multifunctional RT-HRV monitor 10. The display 30 may present various windows, each illustrating the HRV data in a different manner. For example, window 32 shows the heart rate spectrum of the subject 5. A detailed view of window 32 is shown in FIG. 6.

Portions of the frequency range are known to be associated with different portions of the nervous System. In particular, it is noted that the frequency ranges of RT-HRV information on an RT-HRV graph 32 are tightly defined and set forth by international medical organizations and has become the medical standard which is internationally adopted set forth by the European Task Force. These standards are the American Heart Association and the American Association of Cardiac Pacing. Hence, devices in accordance with international norms may be used in various embodiments to measure the SNS and PSNS components of the ANS, such as may be derived, for example, by monitoring the heart of the subject. This SNS and PSNS data may be automatically calculated by the computer program 26 in accordance with, for example, Task Force Protocols, and then used to determine if the subject has reached a state of homeostasis. Specifically, frequencies from about 0.03 to 0.13 Hz are associated with the sympathetic nervous system (SNS) and frequencies from about 0.13 to 0.38 are associated with the parasympathetic nervous system (PSNS) Hence, the SNS components of the HRV data may be shown in one color or format 321, while the PSNS components may be shown in another color or format 322, as shown in FIG. 6.

Figure 7:
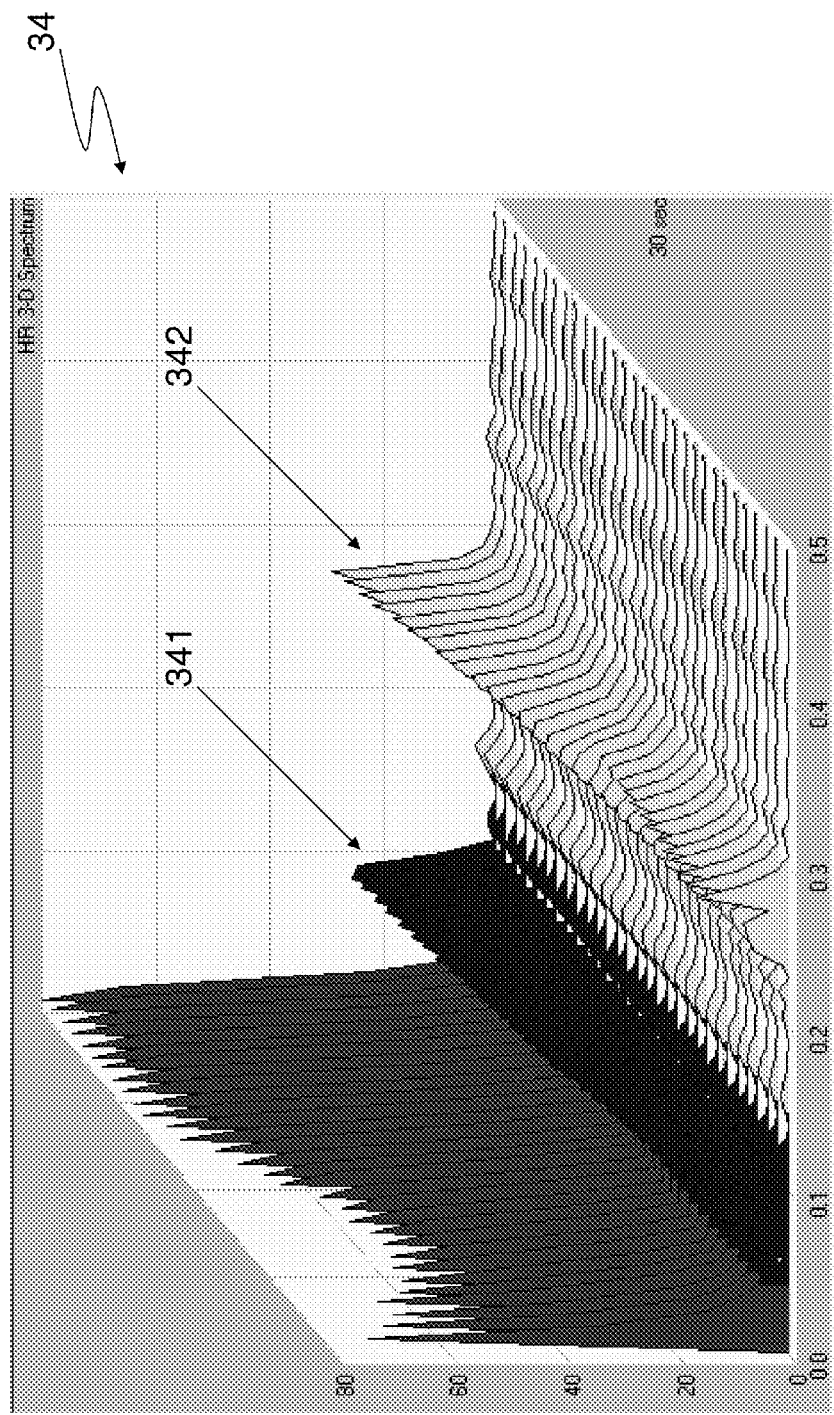
FIG. 7 is a detailed view of a window in the embodiment display shown in FIG. 2 showing 3-D heart rate spectrum data.

Embodiment computer systems 20 may include various user interfaces to display the SNS and PSNS data. Suitable program code within the computer program 26 may be designed, using conventional techniques, to provide the desired visual output on a user-interface of the display 30. For example, FIG. 7 is a detailed view of window 34 on display 30 that provides a 3-D spectrum showing the HRV data accumulated over 30 seconds. Summing the SNS and PSNS portions of the thirty or so spectra along the time axis yields a volume for the SNS portion 341 and PSNS portion 342 instead of the areas shown in FIG. 6.

Figure 3:
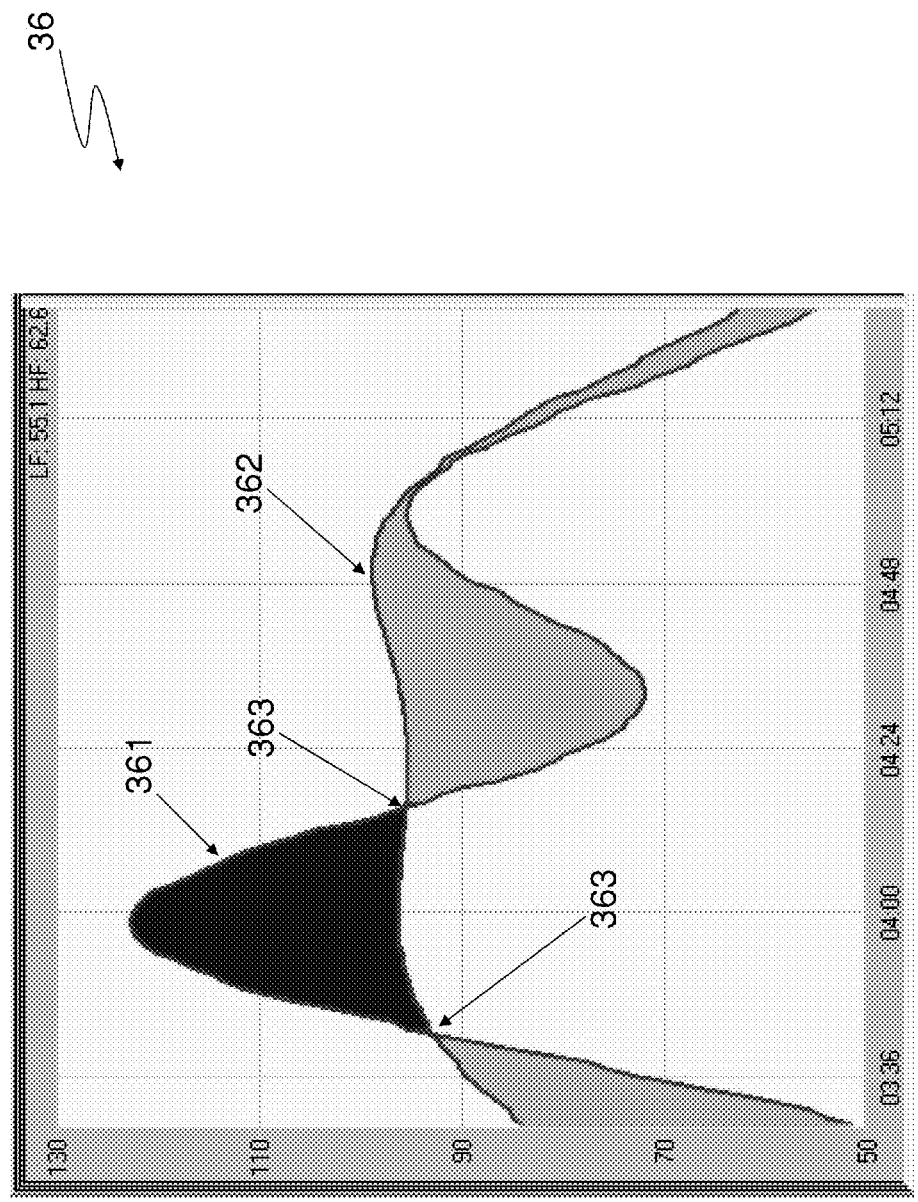
FIG. 3 is a detailed view of a window in the embodiment display shown in FIG. 2 showing ANS activity and cross-over events.
Figure 4:
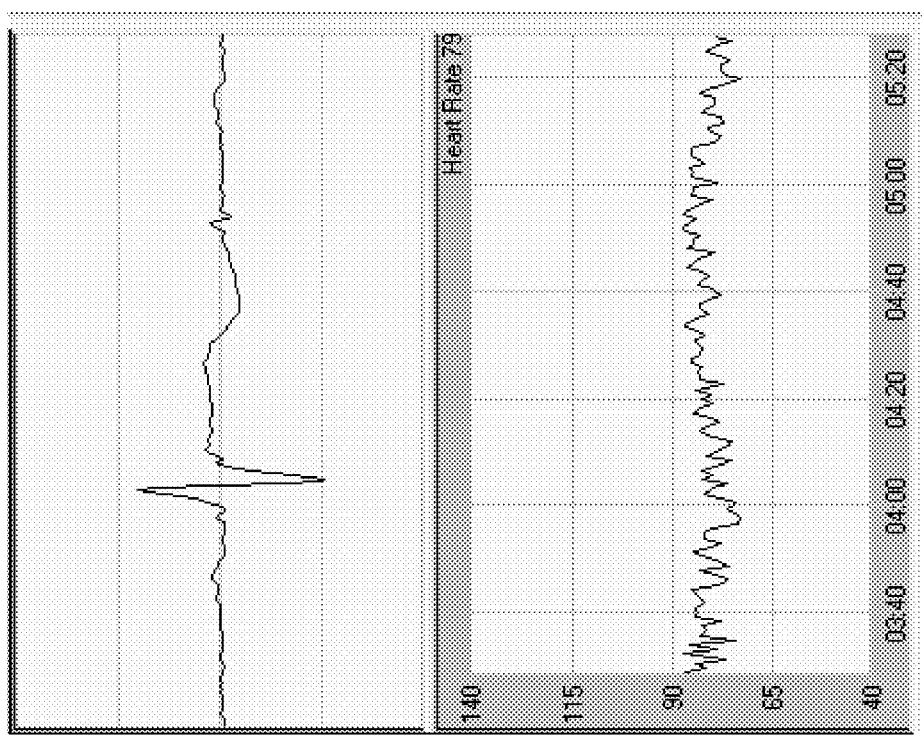
FIG. 4 is a detailed view of a window in the embodiment display shown in FIG. 2 showing moment-by-moment heart rate activity.

For various embodiments it may be desirable to see the ratio of sympathetic (SNS) to parasympathetic (PSNS) activity to determine when homeostasis is achieved within the subject 5; window 36, for example, may be provided to indicate such a ratio. A detailed view of window 36 is shown in FIG. 3. Dominance of the SNS may be indicated, for example, by a region 361 of one color, while dominance of the PSNS may be indicated by a region 362 of another color. Where the SNS 361 and PSNS 362 components are in balance may be indicated by a cross-over point 363. This cross-over point 363 represents a zero-stress point of the ANS and a maximum balance or coherence of the homeostasis point, which occurs when the ratio of the SNS component to the PSNS component is from about 0.90 to 1.10, and more preferably from 0.95 to 1.05, and is ideally about 1.0.

Figure 5:
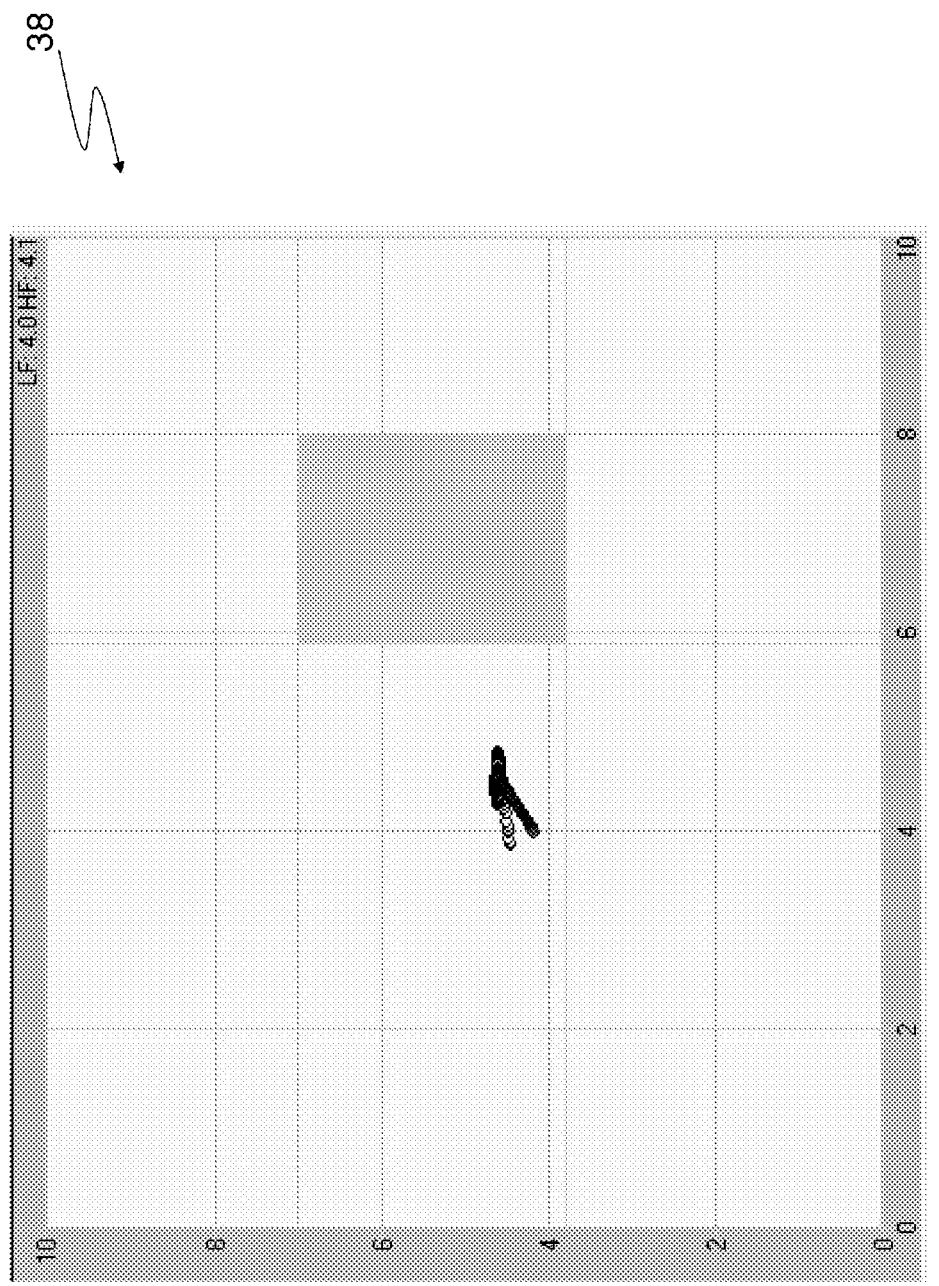
FIG. 5 is a detailed view of a window in the embodiment display shown in FIG. 2 showing a scatter plot of ANS activity over the last 30 seconds.

A scatter plot may also be desirable that shows the last 30 seconds, for example, of ANS activity to illustrate where the subject 5 is in relation to an impending homeostasis crossover event 363 as well as all cross-over events 363 from when a session starts; window 38 may be provided to illustrate such scatter-plot data. A detailed view of window 38 is shown in FIG. 5. A line drawn from the lower left corner of the window (which may be the 0-0 point of the axis) to the upper right corner of the window 38 (which may be the 10-10 point of the axis) represents the line of perfect balance of the ANS at various amplitudes of power of the heart rate, and thus corresponds to a cross-over event 363 shown in FIG. 3.

Yet other embodiments may provide a real-time HRV bandwidth display that shows the real-time Very Low Frequency (VLF), Low Frequency (LF) and High Frequency (HF) bands, and a 3-D "waterfall" display of the last 30 seconds, for example, to see at a glance the progress of the ANS balance. The computer program 26 may be designed to provide such displays, using conventional graphical and data processing techniques known in the art.

FIG. 7 shows the sympathetic function 341 and the parasympathetic function 342. In homeostasis, the volumes of the sympathetic functions 341 and parasympathetic functions 342 are substantially equal. Because this may be difficult to "eyeball," the computer program 26 may provide the window 36 as shown in FIG. 3 that shows the real relationship of the SNS 361 and PSNS 362 functions in real-time. As discussed above, FIG. 3 presents the ratio of the SNS and PSNS ANS components derived from the HRV data, and illustrates crossovers 363 of SNS/PSNS functions at times in minutes:seconds of about 3:37 and 4:23, i.e., when the ratio of SNS to PSNS activity is approximately equal, a zero-stress point of homeostasis. Normally a subject 5 lying supine for three to five minutes should have the ANS reach this zero-stress point or point of homeostasis 363. An abnormal response would be a persistence of SNS 361 or PSNS 362 functional dominance. Chronically stressed individuals, human and animal alike, exhibit a dominant SNS 361 with no SNS/PSNS interaction/crossover 363 occurrence. The same is true with those who have few if any coping skills left and are in a chronic state of PSNS activity 362, which can have results as equally debilitating as those seen when the SNS state 361 is chronically present.

Research has shown that the frequency or amplitude of rhythmic body processes, such as breathing, pulse rates, brain wave frequencies, etc., can be influenced and even controlled by external stimuli. This phenomenon is called "entrainment," meaning that an external stimulus draws the frequency of the body process toward the frequency of the stimulus.

The human and animal brain creates electrical impulses with characteristic frequencies. The frequencies of these brainwaves can be altered, that is, entrained, by using an external stimulus such as sound or flashing lights, having a frequency in the range of typical brainwaves. It has been found that brain frequency entrainment is more effective if the entraining frequency is presented indirectly in the form of a "difference frequency."

When two tones with slightly different frequencies are presented in the form of audible, that is, air-borne sound, the "difference frequency" is generated in the air by physical interference of the compression waves in the air. This phenomenon is often noticed in the sound of two musical instruments played together but at frequencies a few Hertz apart, or the sound of a twin engine airplane, and may be termed a beat frequency or a binaural beat.

With the use of headphones, the frequencies of two tones cannot be perceived as separate tones by the two hemispheres of the brain when these tones are tuned to each other within a critical bandwidth of each other. The critical bandwidth is the maximum frequency difference between two tones that cannot be distinguished by the subject 5. The critical bandwidth is typically a difference of 18% or less between the two tones. When the difference in frequencies of the two tones is within the critical bandwidth (i.e., 18% or less), the left and right hemispheres of the brain compare the received frequencies and generate a "difference frequency," that is, a third frequency that is the mathematical difference between the two frequencies. This act of comparing and cooperation of the right and left hemispheres of the brain can have a beneficial effect upon the brain, helping the two hemispheres of the brain to become synchronized and operate at more equal strengths. The brainwaves also become "entrained" to that generated beat frequency, inducing a desired state of consciousness, such as relaxation, sleep, creativity, peak performance, etc. Therefore, with the use of headphones, brainwave entrainment plus brain hemisphere synchronicity responses may be obtained.

In contrast to headphones, speakers may also be used, in which each speaker plays a tone that is different but within the critical bandwidth with respect to the other. For example, the left speaker may play a 100 Hz tone and the right speaker may play a 105 Hz tone. The tuning of these two tones is close enough to one another to be within the 18% critical bandwidth. Air pressure waves from the two speakers cause a collision of air molecules in the room space between the speakers, which is heard as a pulse. The frequency of this pulse (i.e., the beat frequency) is the difference between the two frequencies, and in this case would yield a 5 Hz beat or pulse. If one speaker is turned off only the single tone of the other speaker would be heard, without the pulse or beat. With headphones, on the other hand, neither ear can hear what the other ear is hearing. The right hemisphere of the brain processes information from the opposite, left hemisphere and vice-versa with the opposite ear/hemisphere. This arrangement provided by headphones forces the brain to synchronize the electrical activity of the two hemispheres, which then manufactures the difference between the two tones as a perceived pulse of 5 Hz, when in reality there is no pulse at all except a moment by moment mental construction. This is not so with the use of speakers. With speakers, the modulated pulse in the room is an actual physical phenomenon of the collision of air molecules in the room driven by the interaction of the air pressure waves coming from each speaker. In addition, there is a lot of "cross-talk" in the room. This means each ear can hear what the other ear is hearing to some extent and so hemisphere synchronization is not something which is forced to happen. The hemisphere synchronization is a phenomenon of the use of headphones where each ear is sufficiently separated from the other in what is heard. With the use of external speakers alone, there is only the entrainment response in the brain and no synchronicity. Hence, some embodiments may only induce entrainment of the subject, whereas others may induce both entrainment and synchronicity within the subject.

However, in some embodiments it may be possible to produce both entrainment and synchronicity within a subject using only speakers. For such embodiments, a soundtrack is provided in which the data from the left speaker is layered in the right speaker 180 degrees out-of-phase (and vice-versa with opposite speaker sounds), which causes a phase cancellation of that sound in the opposite ear. In this way, if the subject is directly between the speakers, each ear is technologically blocked, by way of phase cancellation, from hearing what the other ear is hearing, "cross-talk" is eliminated and hemisphere synchronicity is induced, which can be shown using, for example, a standard EEG. For example, a speaker system may have a left channel L and right channel R. Two tones may then be selected that are within the critical bandwidth of each other, one being tone A the other tone B. Two other tones are then created, using for example standard signal processing techniques, that are identical to A and B but 180 degrees out of phase with A and B, and are tone A* and tone B*, respectively. Using standard signal mixing techniques, channel R plays a combined tone A+B* while channel L plays the combined tone B+A*. The subject is then positioned so that the midpoint of a line between the ears of the subject is substantially aligned onto the midpoint of the line between the speakers L and R.

Other stimuli often used for this purpose of entrainment include flickering light or acoustic vibration, which is vibration of a physical medium at a frequency within the range of 20 to 20,000 Hertz. Acoustic vibration may be vibration of the air that can be heard with the ears (audible), or vibration of a solid support surface that is felt by the body and transmitted to the brain without traveling through the auditory nerves (tactile).

It has been found that a highly effective means of brainwave entrainment is to support a body on a solid or body support surface that includes a split resonator, as disclosed in application Ser. No. 10/893,077, filed on Jul. 17, 2004, and entitled "Sound delivery system for vibro-acoustic treatment," the contents of which are incorporated herein by reference. Briefly, each half of the resonator is vibrated at a different frequency by sounds driving a set of transducers by means of an amplifier. The halves of the resonator are acoustically separated so that vibrations do not cross from one half to the other. In this manner, each half of a body feels vibrations that are communicated to its respective brain hemisphere enabling the brain hemispheres to entrain and synchronize. In this case the synchronicity is occurring in the vibration-sense processing centers of the brainstem and cortex.

Similarly, entrainment and synchronization may be possible by way of light stimulation, which may cause responses in the visual cortex areas of the right/left hemispheres as well. To this end, an embodiment device may translate the frequency activity of sounds into light pulse flickers in a pair of eyeglass or eye goggles. By way of example, embodiment glasses are wired with small light emitting diode (LED) light clusters on the right and left lenses. The right/left clusters are respectively driven by the corresponding right/left sound channels from any sound source (such as a provided by a CD, MP3, etc.) thereby causing the lights to flicker as the sounds fluctuate, becoming brighter or dimmer as the sounds get louder or softer, using any suitable electronics, such as operational amplifiers using the audio signal channels as an input to drive the respective groups of LEDs. In preferred embodiments, using standard electronics the glasses or goggles can be set to a variety of modes from being frequency driven to amplitude driven or combinations of the two. It will be appreciated that if the glasses are driven in the frequency domain that it is possible to set limits to the bandwidths displayed, such as by using standard bandpass filters; for example, certain embodiment bandpass filters may only permit relatively low-frequency signals to drive the LEDs, such as frequencies that are within the response time of the eyes of the subject 5; in humans this may be, for example, frequencies less than about 60 Hz. In accordance with various embodiments, specifically designed soundtracks may be provided to drive the lights in a desired manner. Such soundtracks may be configured such that the above-described binaural beats are generated; that is, by way of example, the left and right channels may be tuned to different frequencies that are within the critical bandwidth of each other to generate a binaural beat of a desired frequency. The brainwave entrainment pulses built into these soundtracks with binaural beats cause the right and left eyes to translate the binaural beats for a visual cortex entrainment and right/left visual cortex synchronicity. The soundtracks may be pre-made, such as in the form of a CD, or may be generated on the fly, for example, by the computer system 20. For example, the computer system 20 may include audio driver circuitry 28 as known in the art that is controllable by the CPU 22. The audio circuitry 28 may include at least two channels, such as a left and right channel, that the CPU 22 can control independently to output desired frequencies and volumes on each channel. The program 26 may direct the CPU 22 to cause the audio driver 28 to output frequencies, volumes, volume fluctuations and combinations thereof on each channel to generate the desired binaural beat or beats for the LEDs. Using standard coupling techniques, such as a cable or a wireless connection, the output of the audio driver may be fed as input signal to an embodiment frequency application device 40, such as goggles 44. This input signal then determines the frequency or frequencies of the external stimulus that the frequency application device 40 imparts to the subject 5.

In preferred embodiments the auditory cortex is synchronized through headphones 42 with the visual cortex by the simultaneous use of embodiment glasses or goggles 44. Both frequency application devices 42, 44 may be driven by the same output from the audio driver 28, for example. Hence, the same sound track that drives the headphones 42 is also used to drive the embodiment goggles or glasses 44. Simultaneous use of headphones 42 and embodiment light glasses or goggles 44 results in a new and more inclusive entrainment and synchronicity phenomenon in the brain in which the temporal lobes (sound processing areas) and occipital lobes (visual processing areas) synchronize with one another in addition to having the right/left hemispheres of each synchronize right/left hemispheres. A subject 5 is now "seeing what they are hearing."

In a particularly preferred embodiment treatment method, the further use of the above-described embodiment body support surface 46 having mutually isolated left/right vibration surfaces is employed to synchronize the right and left brainstem areas that process the vibration sense with the visual and auditory cortex areas in a three-way synchronicity event in the nervous system. Hence, an embodiment body support surface 46, embodiment goggles 44 and headphones 42 may be employed with the same subject 5, the left and right channels of each frequency application device 42, 44, 46 being respectively driven by the same audio track, such as by the output of the audio driver 28 as controlled by the computing system 20.

Sound vibration frequencies below 500 Hz, through embodiment body support devices 46 are transmitted from skin sensor cell bundles to the posterior tracks of the spinal cord (which specialize in transmitting vibration sense information), up to specific areas of the brainstem where they are processed before routing to the brain. The spinal cord is also divided along left and right sides as well. By separating the sounding boards of the body support devices 46 into right/left sides, "headphones for the body" are created. Binaural sounds coming through the right/left separated sounding boards of an embodiment body support device 46 now force the right/left brainstem processing areas of the brainstem to synchronize their activity in the same manner as the auditory cortex and visual cortex. The subject 5 is thus "seeing what they are hearing and what they are feeling." A synchronicity event is thus achieved in the three primary perception systems of the brain: visual, auditory and kinesthetic.

Of particular relevance to the various disclosed embodiment frequency application devices 42, 44, 46 is the frequencies at which the channels in the devices 42, 44, 46 are to operate. It is generally known that certain ranges of brainwave frequencies are associated with particular mental or emotional states, such as concentration, wakefulness or sleep, to mention a few.

It is known that a treatment stimulus having a frequency corresponding to the frequency of a particular brain state can cause a brain to entrain and begin operating in that entrained state, and thus place the subject into a desired state or condition. It is also true that octaves of that particular frequency are effective in changing the brain state.

In various embodiments, the desired response of a subject 5 is the balancing of the ANS into a state of homeostasis, wherein the SNS and the PSNS are interactively in balance. It has been found that exposure of the ANS to a specific frequency, known as the fundamental frequency, which varies from individual to individual, can place the ANS into a state of homeostasis. When in this state, the graph of the ratio of the SNS and the PSNS components of the ANS, for example and as shown in FIG. 3, weaves back and forth across the zero-stress or homeostasis points 363.

Precise brain frequencies vary in different individuals and may vary over time within a single individual or animal. Therefore, finding the effective frequency to induce a desired state, such as the fundamental frequency, generally requires trial and error to find the optimum frequency. By way of example, to find effective frequencies, a signal generator, such as the audio driver 28, can supply various frequencies to an embodiment device 40 and an individual 5 can report when an effect is felt. This process, however, is time-consuming for one scanning the frequencies and noting results. Also, the effects reported by an individual are subjective and may be influenced by the individual's mood at the moment.

As noted above, an individual experiencing the frequencies may be able to report general feelings of alertness, relaxation, and the like, though the self-conscious effort required for doing so distorts or slows the process of frequency selection. Because the individual must necessarily report subjective impressions instead of quantitative data, there may be a large range of uncertainty in the selection and in the long-term effectiveness of the frequency selected. Another disadvantage of selecting a treatment frequency based upon verbal feedback is that the condition of homeostasis is difficult for one to recognize and report and also limits a care modality for those unable to speak and select, such as children, seriously ill individuals, impaired functioning individuals and animals. It may thus be desirable to be able to repeatably, accurately and objectively find the optimum frequency, and in particular the fundamental frequency, for a subject in need of treatment, be it human, animal or otherwise.

Standardized monitoring equipment 10 is preferably employed with the subject 5 to give objective findings of which exact frequency causes a balance of the SNS and PSNS branches of the subject's ANS, creating a point of homeostasis 363 for the subject 5. To this end, any device 10 that measures the SNS and PSNS components of the ANS may be beneficially employed, as discussed in the following. By way of a specific example, an RT-HRV monitor 10 as previously discussed may be employed to quickly determine if a subject 5 has a normal reactive ANS. Other devices may be employed, however, such as an EEG device or any other suitable device known or later discovered, which is capable of monitoring and reporting the SNS and PSNS components of the ANS of the subject 5.

As previously indicated, an average, normally healthy person should show a decrease in sympathetic tone to a zero stress homeostasis point 363 within three to five minutes after lying supine (face up) on an exam table. The RT-HRV 10 read-out should show the sympathetic dominant trace 361 collapse down to zero and equalize with the parasympathetic 362 within this three to five minute time span. If after five or more minutes the sympathetic tone 361 is unchanged, this may be clinical evidence of an abnormal functional chronic state of stress. The majority of individuals in the highly industrialized world exhibit such a response. Various embodiments thus employ real-time monitoring of the functioning ANS, such as with an RT-HRV 10, as a tool to find the fundamental frequency that causes the ANS to relax into a homeostasis state and remain there as long as this tone or frequency is playing. Typically, when the proper fundamental frequency for the subject 5 is played, such as through one or more of the frequency application devices 40, the ANS will react within one second or less to achieve a state of homeostasis, as reflected by a cross-over event 363.

Because advance knowledge of which frequency will cause the desired response may not be available, a sweep of a frequency band may be employed, and the ANS is then monitored for a response as the frequency sweep approaches the correct frequency for this subject. This frequency sweep may be administered, for example, through any of the frequency application devices 40 disclosed, and thus may include sweeps provided by sound energy, vibrational energy, light energy or combinations thereof. In various embodiments, during the sweep both channels of the frequency application device 40 may play or utilize the exact same frequency or sound signal. The fundamental frequency is discovered by exposing the subject 5, such as a human, to a sweep of a frequency band that is known to amply cover all possible ranges of the fundamental frequency, including frequencies multiple octaves above and below the fundamental frequency. In humans this is between about 50 Hz and 200 Hz. For non-human subjects 5 the HRV bandwidths for each animal is different but is available in veterinarian libraries. The sweep is preferably performed in steps as small at 0.01 Hz. The frequencies which drive the ANS to the zero crossing point 363, as recorded for example by the RT-HRV 10, are noted, which represent the state of homeostasis. A sweep from 50 Hz to 200 Hz may be performed, for example, over two minutes, and then a return sweep from 200 Hz to 50 Hz may be performed over another two minutes, providing a total sweep time of four minutes. The subject 5 may be exposed to the range of frequencies in wave, sine, square or saw tooth wave form(s), or in any known or currently unknown auditory form(s) deemed most appropriate for the organism, and in any combination thereof.

As the frequency sweep progresses, the ANS responds accordingly. As the frequency sweep approaches the optimal frequency, the sympathetic dominance 361 begins to collapse down until it reaches the zero stress point 363 of homeostasis, where sympathetic 361 and parasympathetic 362 responses are substantially equalized and neither is dominant. At this point the corresponding frequency is marked that is associated with causing this homeostasis event 363. For example, this frequency may be stored in the memory 24 of the computer system 20. The marked frequency may then be spectral analyzed to obtain a readout of the exact frequency and its music or keyboard notation, i.e.: 185.352 Hz or G#+23 cents (G#+23 divisions out of 100 sharp). Playing this frequency or tone through an embodiment device 40, such as a sound table 46, will cause the ANS to achieve its homeostasis point 363 at zero stress in the nervous system. Also, playing this tone through headphones 42 or through the eyeglasses 44 as light modulations of this tone will cause the homeostasis event 363. Combining together the sound table 46, headphones 42 and eyeglasses 44 causes a more compounded effect through aligning and synchronizing various centers in the cortex and brainstem as well as a direct full-body low frequency massage of body tissues.

It will be appreciated that the frequency at which homeostasis is achieved, the fundamental frequency, may vary from species to species. For instance, horses, dogs, cats and all vertebrates can be measured with a suitable device, such as the RT-HRV device 10, the same as human beings; however, the frequency bandwidths for sympathetic 361 and parasympathetic 362 components of the ANS may have different ranges for each of these species. As indicated earlier, these frequency bandwidths are known, so it is just a matter of the instrumentation to have the ability to switch to these different ranges and pre-sets. Non-vertebrate aquatic animals and plants may require a different monitoring system that is also a known to the professionals that work with these creatures.

Because the effect of the above-disclosed acoustic, vibrational or light therapy is not necessarily constant with time, the homeostasis crossover point may undergo further calculations to be precise to the second or micro-second. More specifically, as a treatment progresses using the fundamental frequency and monitoring the response of the ANS with the RT-HRV 10, the needs of the moment for the subject 5 occasionally fluctuate and the homeostasis point 363 is lost. Recapturing the homeostasis point 363 requires a micro-tuning of the sound frequency being used by single cent increments. A "cent" may be a single interval in 100 steps between two immediately adjacent notes on a keyboard, or may be an even finer-grained interval, such as can be obtained with a digital configuration as provided by the computing system 20. This "micro-tuning" is used until the new tuning of the fundamental tone is found which causes the ANS to become balanced again. This tuning is usually within a few cents of the originally-found fundamental frequency. The response will be seen as a return to the homeostasis cross-over configuration 363 of the ANS.

The above-described embodiment methods search for the fundamental frequency, which causes the homeostasis event. When a subject 5 is exposed to this fundamental frequency over time in a therapy session the ANS may respond by going into a rhythmic oscillation pattern where sympathetic 361 and parasympathetic 363 modes exchange dominance as they oscillate across the homeostasis cross-over point 363. The body is living and dynamic and, therefore, rhythmically reacts to the appropriate fundamental frequency. During the first few treatment sessions this pattern may be more disorganized, but improves over time and with continuing sessions. Hence, it is possible to determine how a subject 5 is progressing by monitoring how the ANS responds to the fundamental frequency with time; that is, by monitoring the regularity of the periodicity of these cross-over events 363. Specifically, the ANS should ideally exhibit more even amplitudes of sympathetic 361 and parasympathetic 362 activity in a regular series of cross-over events 363, with a cross-over event 363 occurring once every minute or two for most subjects 5 while in a state of homeostasis. That is, homeostasis may be initially identified by a cross-over event 363, but homeostasis generally is characterized in a substantially regular, rhythmic cycling of the SNS and PSNS components, such that a cross-over event occurs once every minute or two. Occasionally, this cross-over rhythm unravels and becomes a large dominant sympathetic 361 or parasympathetic 362 trace. For most subjects 5 this returns to the desired rhythmic pattern within about 20 seconds. If the ANS does not return to an even-oscillating rhythmic pattern, the application frequency (i.e., the acoustic, vibrational or light-flickering frequencies) can be micro-tuned to bring the system back to the homeostasis rhythm.

Micro-tuning of the fundamental frequency is an embodiment method employed to reestablish homeostasis in the subject 5. As explained above, when in homeostasis the subject 5 exhibits a rhythmic series of cross-over events 363 of the SNS 361 and PSNS 362 components in a substantially regular time interval, which for humans is typically between 1.0 to two minute intervals, and more typically between 1.5 to 2.0 minute intervals. That is, the cross-over event 363 for a human in homeostasis will most typically occur every 1.5 to two minutes. A predetermined "time-out" period is selected based upon the subject 5 that is larger than the typical maximum period of the homeostasis rhythm for that subject 5. For example, in humans the maximum homeostasis rhythm period is about two minutes and so a predetermined time-period of, for example, 2.0 minutes, 2.5 minutes, 3.0 minutes, 3.5 minutes, 4.0 minutes or longer may be employed. If either of the sympathetic trace 361 or parasympathetic trace 362 becomes completely dominant for a period that exceeds the time-out period then it is assumed that the subject 5 is no longer in homeostasis. Micro-tuning is then employed to find the new fundamental frequency and to reestablish homeostasis in the subject 5.

More specifically, it has been determined that there may be a homeostasis zone of frequencies that are beneficial for an individual subject, but only one exact frequency in this zone may be applicable at a particular moment for the subject. This bandwidth of micro-tuning tones may be different for each subject, but statistically is generally within 1 to 10 cents of the originally-found fundamental frequency. When micro-tuning to reestablish homeostasis and to find the resultant new fundamental frequency, embodiment methods search, for example, a cent at a time five cents above the fundamental frequency and, if homeostasis is not achieved, then search a cent at a time five cents below the fundamental frequency. When homeostasis is achieved, the new, micro-tuned frequency may be recorded, such as in the memory 24 and used as the basis for any subsequent micro-tuning procedures. For example, if the fundamental frequency was F#+23 (i.e., 23 cent intervals above F#) and the sympathetic/parasympathetic cross-over 363 regularity unraveled 26 and became sympathetic dominant, it is possible to bring it back to the stable homeostasis configuration of regular sympathetic/parasympathetic cross-over events 363 by micro-tuning the sound to, for example, F#+24, F#+25, F#+26, etc., until the ANS responds by re-achieving the stable cross-over homeostasis configuration.

More generally, when performing micro-tuning the width of the homeostasis zone of the subject 5 is determined, such as by the type of the subject 5. As noted, different species may have different zone widths. In humans it may be about 10 cents in width, but the widths of other species may be obtained or experimentally determined. A database of homeostasis zone widths based upon subject 5 type may be stored, for example, in the memory 24. Variations of the fundamental frequency in one-cent intervals within this zone width are then applied to the subject 5 until homeostasis is reestablished, and this new fundamental frequency is recorded.

Hence, embodiment treatment methods may include an initial frequency sweep across the entire frequency band of the subject to initially find the fundamental frequency of that subject. Then, embodiment methods may continually monitor the SNS and PSNS components of the ANS while applying this fundamental frequency. While an even, rhythmic oscillating of the SNS and PSNS components is monitored, as determined by the time-out interval for that subject, the same fundamental frequency may be applied. However, if while monitoring it is determined that either one of the ANS components is becoming dominant over time, micro-tuning of the application frequency may be performed to find the new fundamental frequency of the subject. It will be appreciated that both the initial frequency sweep, monitoring, and micro-tuning steps may be automated by way of the computer program 26, with the computer 20 processing the HRV data, recording and time-stamping cross-over events 363, the relative strengths of the SNS and PSNS components, monitoring time elapses between such cross-over events 363, and controlling the audio driver 28 to apply the fundamental frequency to embodiment device(s) 40, or micro-tuned variations thereof, as determined by subject specific data held within a database in the memory 24.

In some rare cases a complete 100% cross-over 363 cannot be achieved with modification of the fundamental frequency in cents. In these cases homeostatic cross-over 363 may be achieved by the addition of a harmonic, e.g., the harmonic 5th tone of the fundamental frequency, to the mix and the ANS then comes into a state of balance. Standard signal-processing methods and software may be employed by the computer program 26 to generate such a mixed-frequency tone via the audio driver 28. In ensuing sessions, it may no longer be necessary to add these one or more harmonic frequencies. Hence, in some embodiment methods and related systems, if micro-tuning by adding cents to or subtracting cents from the fundamental frequency does not cause any change, that is, all single-cent increments of frequencies within the micro-tuning bandwidth do not yield the desired cross-over event 363, both in positive and negative directions, then the addition of one or more harmonic frequencies, such as a harmonic 5th tone, can sometimes be the key to get the ANS to respond in a more balanced manner. If all methods fail, then the session may be terminated, as this almost always means the subject 5 has achieved all the re-training it can handle at that time.

It has been found that there is a direct relationship between the fundamental frequency, and any octave of the fundamental frequency, and achieving homeostasis in the ANS. For purposes of the following, an "octave" includes both the doubling of a frequency and the halving of a frequency to create an octave of that frequency. In contrast, other integer multiples of a frequency, such as 3, 5, 6, 7, etc., are called "harmonics" of that frequency. As in acoustic physics, where any octave of a correct tone will cause a specific wine glass tuned to that tone to go into a special state of resonance, a similar effect is observed with the ANS. Once fire fundamental frequency that causes the ANS to achieve homeostasis is found, any octave of this fundamental frequency will cause the homeostasis event in the ANS. By calculating lower octaves of the fundamental frequency so that the calculations pass below 20 Hz (the lower threshold of human hearing), it is possible to calculate a string of lower octaves that correspond to highly specific brainwave frequency states of consciousness. Some of these better-known brainwave frequencies are in the Beta (13 to 30 Hz), Alpha (7 to 13 Hz), Theta (3.5 to 7 Hz), and Delta (0.5 to 3.5 Hz) frequency ranges. Epsilon frequencies are below 0.5 Hz.

Use of the fundamental frequency to regulate the ANS to a homeostatic state may be supplemented by the use of binaural beats to entrain brain waves which are methodology-integrated through phase modulation. As previously described, phase modulation is a means for stimulating the two brain hemispheres of the subject separately with different frequencies of acoustic vibration to set up a binaural beat at a frequency that is the mathematical difference between the two frequencies. This includes the acoustic vibration of the right/left body halves of the entity with low frequency vibration sense, the use of headphones to present a different frequency to each of the entity's ears, or the use of goggles, all as earlier described.

Using binaural beats set to any of these "octave brainwave states" will cause a homeostasis event in the ANS just as if the fundamental frequency were played through a frequency application device 40. For example, if the frequency fundamental frequency of the subject was found to be 234.56 Hz, the lower octaves of this fundamental frequency would be: 117.28, 8.64, 29.32, 14.66, 7.33, 3.665, 1.8375, 0.91625, 0.458125, 0.2790625 Hz, etc. Since the lowest range of human hearing is 20 Hz, all frequencies identified below this range are in the realm of brainwave frequencies in Beta, Alpha, Theta, Delta, Epsilon, etc. Since any octave of the correct fundamental frequency causes the cross-over homeostasis event 363 in the ANS, these identified brainwave frequencies should also work as well, since they are all perfect octaves of the fundamental frequency. Therefore, configuring the audio output driving an embodiment device, such as the frequency application device 40, to generate binaural beats set to, for instance, 7.33 Hz Theta from the example above, without necessarily using sound tones playing the fundamental frequency itself in any of the audible ranges, may cause homeostasis in the ANS from simply the specific brainwave state to which the binaural beats have entrained the brain. In this example, when the brainwaves are entrained to 7.33 Hz, the same homeostasis event happens in the ANS as it would if the fundamental time were played through an embodiment frequency application device 40. Such embodiment methods "pick the lock" of a neuro-program using this highly specific brainwave entrainment frequency.

Other embodiments may also employ higher octaves of the fundamental frequency to induce homeostasis. Preferred embodiments employ the fundamental frequency itself in combination with a plurality of octaves of the fundamental frequency, such as two octaves above and two octaves below, all of which are combined into a multi-frequency tone that is administered to the subject via one or more of the frequency application devices 40. A particularly preferred embodiment will further employ a binaural beat frequency mixed into this multi frequency tone. The binaural beat is preferably an octave of the fundamental frequency that is within a selected brainwave frequency domain in which entrainment is desired, such as the Beta, Alpha, Theta, Delta, Epsilon, etc., state. To create such a binaural beat a foundation frequency is first selected, which may be any frequency suitable for the specific frequency application device 40 employed. This foundation frequency is mixed together with the multi-frequency tone into one channel of the device 40. A second frequency is then mixed with the multi-frequency tone in the other channel, in which the difference between the foundation frequency and the second frequency equals the desired beat frequency, which is the target brainwave frequency. Hence, both channels of the device 40 play the multi-frequency tone, but they further respectively play one of two frequencies that, when combined, produced the desired beat frequency to cause entrainment with the target brainwave. Of course, it will be appreciated that in some embodiments only the foundation frequency and second frequency are played, without any other frequencies or tones.

In preferred embodiment methods and systems that drive the channels of the frequency application device 40 separately to generate a beat frequency, the foundation frequency employed is itself an octave of the fundamental frequency. In particularly preferred embodiments, the foundation frequency is that octave of the fundamental frequency which is closest to 50 Hz. In a specific embodiment, half the target brainwave frequency (i.e., beat frequency) to entrain to is added to the nearest 50 Hz foundation tone in one stereo channel and half the target brainwave frequency to entrain to is subtracted from the foundation tone and placed in the opposite channel. The target brainwave entrainment frequency is now present, but neither stereo channel has a foundation frequency playing the fundamental frequency or an octave thereof; rather each channel has a plus or minus of that tone by ½ the brainwave frequency to entrain to. In a further refinement, determining which channel gets the added tone (i.e., the higher frequency tone) and which channel gets the subtracted tone (the lower frequency tone) is based upon brain dominance. The higher frequency foundation tone of the binaural beats is placed in the opposite channel of the non-dominant hemisphere and visa-versa; that is, the dominant hemisphere is fed the lower-frequency tone. This is to suppress the dominant hemisphere function and augment the non-dominant hemisphere function and create another synchronicity event between the hemispheres; in this case an event of ambidextrous hemisphere function. By way of continuing the above example, assume we wish to entrain to 7.33 Hz Theta. We chose a foundation tone of 58.64 Hz (which is closest to 50 Hz). We then test for brain dominance and assume that the subject 5 shows a left dominant hemisphere. We therefore subtract half of 7.33 Hz (3.665) from the foundation tone and place it in the right stereo channel (since the left hemisphere processes right ear sounds) to diminish left dominant function and also add half of 7.33 Hz (3.665) to the foundation tone and place it in the left stereo channel to augment the right non-dominant hemisphere function.

Any suitable test known in art may be employed to determine hemisphere dominance. Simply by way of example, the subject 5 may be asked to form a circle with their thumb and index finger and hold it at arm's length, and then to look through this circle with both eyes and focus on the clinician's raised index finger held up a distance away. Then the subject 5 is asked to look with just one eye open and then the other eye. Only one eye will see the clinician's index finger through the circle. This is the dominant eye and its opposite hemisphere is therefore the dominant hemisphere.

By way of the above method, brain dominance is now being equalized and trained over time. In addition, the brain is now in an active phase of manufacturing the brainwave entrainment frequency and then entraining to it. The use of speakers only for entrainment may be a passive entrainment phenomenon. Instead, embodiments combine both together to get active and passive modes to synchronize and work together. In addition a third phenomenon takes place. The brain of the subject 5 will also split the different between the two tones that create the binaural beat and manufacture a new tone which it now hears. Since both binaural beat tones have been offset in tuning from the foundation tone (added to one side and subtracted from the other) the "split the difference" tone the brain now hears in the middle is the true fundamental tone or an octave thereof, which causes ANS homeostasis. In this case this created fundamental tone is actively being created by the brain of the subject 5 as opposed to being passively exposed to it using a tone or multi-frequency tone as described above being played through one or more of the devices 40. Therefore, the brain is being forced to actively participate in manufacturing both the tone which balances the ANS and the associated brainwave state, which also causes homeostasis. This may be a highly beneficial aspect of such embodiments.

From the foregoing description it is clear that there is a specific relationship between the frequency which is associated with causing the homeostasis event in the ANS, i.e., the fundamental frequency, and octave-related brainwave states of consciousness which can be induced through binaural beat brainwave entrainment. It is this relationship among frequencies and octaves of frequencies that is used in embodiment processes to orchestrate the homeostasis event in the ANS, an associated state of consciousness through brainwave entrainment and a multi-system neurological synchronicity of hemispheres, including visual, auditory, and kinesthetic perceptual modes and full body vibrational massage of body tissues.

Particularly preferred embodiment methods use the fundamental frequency or frequencies to interact with the brain to induce the desired beneficial effect of inducing homeostasis in a subject 5. A specific embodiment treatment regimen begins by finding the fundamental frequency for the subject 5. The subject 5 is placed on an embodiment body support surface 46, such as by laying on a sound table or sitting in a sound chair. The RT-HRV sensors 12 are attached to the subject 5. A sound sweep is played through the body-support surface 46 based upon the subject 5; for example, the sweep may be played through two octaves from 50 Hz to 200 Hz and back to 50 Hz in a four minute loop through the body-support sound surface 46, as previously described. The use of multiple octaves may provide, for example, a broader use of the devices 40, which may have differing functionally usable frequency bandwidths. The functional ANS pattern of the subject 5 is monitored, which generally shows an abnormal sympathetic dominant ANS, but can also show an abnormal parasympathetic dominant ANS as well. The response of the subject 5 to the sound sweep tone is monitored as the applied frequency nears the fundamental frequency for that subject 5. As noted, the fundamental frequency is determined when a cross-over event 363 occurs.

The precise fundamental frequency for that subject 5 is identified and processed to create a number of octaves thereof, which may be predetermined or determined on the fly based upon the perceived needs of the subject 5. As an example, if the fundamental frequency is 117.28 Hz, four octaves may be created, such as two octaves above and two octaves below the fundamental frequency, and then these five frequencies (469.12, 234.56, 117.28, 58.64 and 29.32 Hz) may then be played through the body support surface 46 and with headphones 42. Lower brainwave octaves are then calculated, which with specific reference to this example would be: 117.28, 58.64, 29.32, 14.66, 7.33, 3.66, 1.83, 0.915, 0.45 and 0.22 Hz. A first treatment session may then begin by selecting an octave corresponding to a desired brainwave to entrain with, for example with the lowest Delta brainwave octave, which would be the frequency at 0.45 Hz. Note that although standard texts show the lowest Delta to be 0.5 Hz, this is only based on statistical averages on a bell-curve, and hence 20% of the population fall off the edges of the bell curve and don't conform to this range. Thus, the exact determination of brain frequencies may vary from subject 5 to subject 5. For purposes of this example it is assumed that the lowest Delta frequency of the subject 5 is 0.45 Hz. Binaural beats are created as set forth above and set to the desired brainwave frequency range that is an octave of the found fundamental frequency, such as in this case 0.45 Hz. These binaural beats are added into the mix with the five octaves of low frequency sounds coming through the sound table 46, headphones 42 and light glasses 44. In some embodiments, to facilitate the listening experience for the subject 5, formatted sound tracks, such as primordial sound tracks, which are nature sounds such as of the body, animals, space, etc., may be added to the mix. The volume levels of the various octaves and the binaural beats may be adjusted to pleasant listening levels. The HRV data from the RT-HRV device 10 is monitored to make sure that there is an optimal cross-over pattern in the sympathetic/parasympathetic branches of the ANS, as discussed above. Micro-tuning is performed as necessary if the cross-over configuration comes apart, as described above.

In some embodiments a treatment session may last for thirty minutes, unless uncoupling of homeostasis indicates the session should be terminated earlier, as discussed above. In preferred embodiments only one brainwave entrainment frequency is used per session. In such embodiments the next session may use the next brainwave frequency in order, i.e., Delta 1, Delta 2, Delta 3, Theta, then Alpha in successive visits, which may be separated by, for example, a week. In specific embodiments each session is recorded onto a CD and given to the subject at the end of the session to take home and listen to once a day until returning for the next session. Then the next session generates the next CD with the next brain entrainment binaural beat and the subject then uses this 2nd CD for the following period, etc.

Alternate embodiments provide a system 1 that automates the above methods. An embodiment system 1 may include one or more of the frequency-application devices 40 disclosed above, such as a body support surface 46, headphones 42, goggles 44 or combinations thereof. A monitor of the ANS, such as an RT-HRV interface 14 is also provided. A suitably programmed computer obtains ANS related-data from the monitor 14, which may be the actual SNS and PSNS data itself or which may need to be processed in a standard manner to generate the SNS and PSNS components, and controls the frequencies at which the frequency-application device or devices 40 operate. The program 26 may include steps to initially find the fundamental frequency, monitor the ANS components of the subject 5 while applying the fundamental frequency via the frequency-application device(s) 40, micro-tune the fundamental frequency as needed, and in extreme cases add harmonics to the fundamental frequency as needed to place the subject 5 into a steady, rhythmic homeostatic state in which the SNS and PSNS components periodically and evenly oscillate across the cross-over point.

In an embodiment session, the subject is connected to the monitoring device 14 and then, after a predetermined resting period such as three to five minutes, the computer program 26 causes the computer 20 to control the frequency-application device (s) 40 via the audio driver 28 to initiate a frequency band sweep to find the fundamental frequency of the subject. Hence, the computer program 26 may include in the memory 24 a database of subject types and a corresponding list of frequency bands in which to sweep to find the fundamental frequency. For example, an entry for human subjects may indicate a frequency hand spanning from 50 Hz to 200 Hz. This database may further include liar each frequency band the frequency steps to be performed during the sweep for that band; for example, for human subjects the steps may be in increments of 0.01 Hz. The database may also indicate for each frequency band how quickly the sweep should take place across that frequency band, such as two minutes. Based upon this data the computer 20 can control the frequency application device (s) 40 to perform an appropriate frequency sweep of the subject. While the frequency sweep is occurring, the computer program 26 also causes the computer 20 to input and analyze the ANS data generated by monitor 14 to generate real-time SNS and PSNS data. As the frequency sweep occurs, the computer 20 monitors the relative strengths of the SNS and PSNS components and marks the frequency at which the SNS and PSNS components begin to move towards homeostasis. In particular, the program 26 is configured to look for a cross-over event 363. The exact frequency within the frequency band that induces the homeostasis cross-over event 363 in the subject is then recorded in the memory 24 of the computer system 20 as the fundamental frequency for that subject. The program 26 may then cause the computer 20 to calculate a predetermined number of octaves of the fundamental frequency, such as 2, 3, 4, 5, 6, 7, etc., octaves to be played, either above the fundamental frequency, below the fundamental frequency, or combinations thereof. The program 26 may also cause the computer 20 to calculate the appropriate brainwave frequency octaves for the session. It will be appreciated that the computer system 20 database may further include patient-specific data for each of a plurality of patients and that this fundamental frequency may be stored as an entry within such patient-specific data. It will be further appreciated that the any of the databases, including the patient-specific database, may be stored on removable storage media, stored within the internal memory media of the computer 20, or accessed and modified via a network.

In certain embodiments the computer program 26 causes the computer 20 to compute a predetermined number of octaves of the fundamental frequency, such as five different octaves of the fundamental frequency, as discussed above. In preferred embodiments these octaves are set to begin at the lowest identifiable octave within the range of hearing for the subject (for example, the lowest range of human hearing is 20 Hz) and the computer 20 calculates a predetermined number of octaves upward from there, such as from three to seven. The program 26 also causes the computer 20 to calculate an octave of the fundamental frequency that is within a desired brainwave frequency band, as described above. The fundamental frequency is then played in the predetermined number of octaves and combined with one of its octave brainwave frequency counterparts using binaural beats set to entrain the brainwaves to this octave frequency, as previously described. That is, the program causes all channels of the audio driver 28 to play the fundamental frequency together with the predetermined number of its octaves. The program 26 further causes the audio driver 28 to play different frequencies in each of the respective channels that create a beat frequency set to an octave of the fundamental frequency that is within the desired brainwave frequency, preferably using a foundation tone that is itself an octave of the fundamental frequency. These computed frequencies are then used to independently drive the channels of the one or more of the frequency application devices 40 coupled to the subject 5.

The above system 1 links the ANS of the subject 5 directly into an automated biofeedback loop. Changes in the ANS response may dictate a micro-tuning of the fundamental frequency as described above to keep the ANS in its maximum state of homeostasis, which may be automatically detected and performed by the system 1. In this way, the unconscious ANS automatic processing centers are in direct control of the system 1 that is keeping the ANS in tune for a faster, more organic and more instantly responsive system-control approach. The embodiment feedback system 1 connects the unconscious system to itself through the software program 26 that helps the unconscious autonomic system get back in control of itself dynamically with an appropriate tool at its disposal for monitoring a maximally healthy state and adjusting itself to achieve that state automatically. An automatic feedback/feed-in loop is thus created, constantly correcting for changes and variation in the ANS, which includes the brain, and hence body responses. In effect, the ANS tells the embodiment system 1 which frequencies and micro-tuning adjustments are required to achieve and re-educate the ANS itself to enable the dual branches of the ANS to oscillate in a rhythmic homeostatic balance, attaining significant benefit to the participating individual, group or organism.

Generally, once octave calculations from the fundamental frequency that cause homeostasis are made, the entire range of all brainwave frequency octaves to this fundamental frequency may be identified and used to induce homeostasis in the subject. This may include the standard brainwave frequencies of Beta, Alpha, Theta, Delta, as well as additional brain frequencies used for special applications, which may include Gamma (about 40 Hz), HyperGamma (about 100 Hz), Lambda (about 200 Hz), Epsilon (below Delta) (about 0.25 Hz), ½ Epsilon (which may be termed Epsilon 2) (about 0.125 Hz), and novel frequencies termed Default Mode Network 1 (about 0.0625 Hz), DMN 2 (about 0.0312 Hz), DMN 3 (about 0.0156 Hz), and DMN 4 (about 0.078 Hz). Additionally, the borderline states between any two brainwave states may be used, e.g., Beta/Alpha, Alpha/Theta, Theta/Delta, Delta/Epsilon and Epsilon/Lambda, etc. Although exposing the body to low frequency resonance to balance the ANS and brainwave entrainment with phase-modulation are both separately powerful, when precisely aligned together an exponential effect is achieved. In particular, the synchronizing of visual, auditory and kinesthetic perceptual modes is obtained by using the same sounds or frequencies applied to the embodiment devices 40 of the right/left split sound table 46 (the kinesthetic system), the headphones 42, and the light glasses 44. In addition, this causes a synchronicity of the right/left hemispheres of the visual cortex, the auditory cortex and the right/left brainstem vibration sense processing centers. As described earlier, in addition to the fundamental frequency, harmonics of the fundamental frequency may be also utilized.

The Default Mode Network (DMN)

The DMN is a brain synchronizing system that was discovered by accident in 2001 and which was coined in a paper by neuroscientists Marcus Raichle. It was seen using PET scans and MRI studies, which indicated that certain specific regions of the brain showed a powerful synchronized modulation of very slow brainwave activity. These regions showed a great increase of activity when the brain was idle, the mind wandering or during the use of imagination. DMN activity dramatically dropped when a subject was directed to solve a problem, externally attend to a task or concentrate or focus on a problem. The name Default Mode Network was chosen to describe the state the brain returned to as a default functioning mode, when not required to accomplish a task of some kind. The four brain regions involved in this very slow synchronized pulse include the Medial Prefrontal Cortex (the frontal lobe areas of higher reasoning ability), the Posterior Cingulate Cortex (an area at the back of the brain associated with imaginary, visualizing oneself in various situations, and personal memories) and two minor zones to the right and left rear, The Right and Left Inferior Parietal Lobes. The brain regions involved lead researchers to believe that this system is the processing area where the sense of self and sense of context with the external self come together; a self-reference orientation system in which it is possible to imagine and visualize alternate future strategies, outcomes, sense of self and personal meaning, etc. In it deeper sense, these are regions of the cortex in constant and continual strong synchronicity at all times, including when unconscious and even when in a coma. The very slow fluctuating brain rhythm of this system has been measured at around 0.1 Hz and 0.2 Hz with an average brainwave pulse of every 15-20 seconds. This pulse speed coincides with brainwave entrainment frequencies of DMN 1 and DMN 2, which directly affect the DMN. Numerous conditions now seem to be directly associated with problems of synchronicity in the DMN system. A distinct connection of desynchronized DMN function and schizophrenia has been shown. There is also consistent evidence of increased speed of brain pulse in the DMN over the normal bell curve in these individuals. Disturbances in the DMN are closely associated with PTSD and the loss of sense of self and personal orientation in one's world. The DMN may be vulnerable to Alzheimer's disease decades before symptoms or plaque appear.

It is possible to entrain and synchronize the DMN using binaural beats in the same way it is possible to entrain and synchronize the cortex and brain hemispheres. Once the fundamental frequency is identified, calculating all the lower octaves of this frequency will identify the corresponding DMN1 and DMN2 brain frequencies. For example, if the fundamental frequency is 117.28, its octaves are 58.64, 29.32, 14.66, 7.33, 3.66, 1.83, 0.915, 0.45, 0.229, 0.1145, 0.0572 and 0.0286 Hz. In this case, the last two brain states, 0.0572 and 0.0286 Hz, correspond to the identified DMN frequencies. These may be generated as binaural beats for entraining the Medial Prefrontal and Posterior Cingulate Cortex into synchronicity by rotating the binaural beats in 3-D virtual space to match their positions of front/back instead of the right/left configuration of right/left hemispheres. Known audio processing techniques and its related software may be employed to perform this 3-D rotation of the binaural beat. Simply by way of example, software which may be used in the computer system 20 to perform the desired 3-D rotation effect may include Maven 3D Professional Multi-Channel 3D Audio Editor by Emersys Corp. It will be appreciated that exactly which frequencies to employ and how to rotate these frequencies or their related foundation frequencies may depend upon the subject and the desired treatment regimen.

By way of example, brain mapping studies have shown ADD and ADHD children have coordination deficits within a single hemisphere as well as deficits of communication in oblique and diagonal planes between hemisphere, for example between the right frontal and left occipital brain hemisphere regions. An embodiment treatment method for such subjects may employ psychoacoustic 3-D virtual rotation of the binaural beats in three dimensional sound space to match the two tones of the binaural beats to the right frontal and left posterior occipital brain regions to entrain them more effectively. More specifically, children suffering from ADD/ADHD may tend to be "stuck" in mid-range Theta brain activity (from about 7.0 to 3.5 Hz), which is where the brain goes when it is daydreaming. When asked to focus on an external task, the brain waves in such subjects 5 do not increase speed up through Alpha and into the normal Beta brain function (13 to 30 Hz) associated with focused task-oriented brain activity. In addition, the brain hemispheres may not be functionally communicating completely together and even not communicating correctly within a single hemisphere. For instance, there may be a non-communication diagonally between the right frontal zone and the left posterior occipital zone, stuck at 5.0 Hz Theta. For this case, an embodiment process may begin entrainment at 5.0 Hz and instantly cause entrainment because the process is entraining to what the brain of the subject 5 is already doing. The binaural beats would be rotated in 3-D space to match the diagonal plane of non-communication for this subject 5. Entrainment would then begin to slowly speed up the brainwave entrainment pulses toward a target frequency, such as a Beta frequency. Thus, in certain embodiments treatment may finally involve, for example, entrainment to the Beta state using appropriate 3-D acoustic rotation as required. For example, 3-D virtual rotation of the binaural beats, which are selected to entrain to the Beta brainwave state, in three dimensional sound space is performed to match the two tones of the binaural beats to the right frontal and left posterior occipital brain regions to entrain them more effectively. In this case, entrainment from where the brain was currently "stuck" as in a 5 Hz Theta, up and out to a higher 14 Hz Beta zone was obtained in a few sessions. Since Beta activity is what the brains of such subjects 5 could not accomplish, entrainment to the Beta states was highly effective.

Other embodiment methods along the same approach may similarly use psychoacoustic 3-D sound rotation of appropriate binaural beats to match the frontal and posterior occipital DMN zones as well as the two auxiliary Parietal Zones in a therapeutic re-synchronization treatment of various conditions associated with dis-synchronization of the DMN. The 3-D rotation of binaural beats set to one of the DMN brain frequencies may be identified by calculating lower octaves of the fundamental frequency of the subject 5, and then the foundations tones may be aligned front and back to match the Frontal and Occipital DMN brain activity cortex zones involved at the front and back areas of the cortex. Secondary binaural beats may also be added at 3-D positions to entrain and synchronize the Partietal lobes on the posterior right left sides of the brain.

For the human and more highly developed living organisms, the guidance given to and orchestrated by the ANS itself will produce benefits known when specific brainwave states are achieved. As disclosed above, entrainment into these desirable brainwave states may be induced by the embodiment methods. These brainwave states include those currently known, such as, Lambda, HyperGamma, Gamma, Beta, Alpha, Theta, Delta, Epsilon and the bridge states of each, including but not limited to the Mu brainwave state required for mirroring and learning from the behavior of others thought lacking in autism and like conditions, as well as those brainwave states possibly yet to be discovered with advancing technology, including the various DMN states.

Binaural stimulation of the brain for purposes of entrainment may also include the use of the subject's own voice singing the fundamental frequency which balances the subject's ANS. The subject's voice is recorded singing a sound similar to the "Ahh" sound at the particular fundamental frequency. It will be appreciated that known audio processing techniques may be employed to frequency-shift the recorded sound onto the desired fundamental frequency, and additional frequency shifts of the recorded sound may further be performed in accordance with any micro-tuning steps. The voice of the subject is a complex sound that is sympathetic to the ANS of the individual. The sound may then be copied to the opposite channel and shifted a mathematical number of Hertz, such that when the two sounds are played in opposite channels, a binaural beat arises, produced by a phase modulation of the sound of the subject's own voice. As set forth above, this beat frequency may be set to an octave of the fundamental frequency.

Although the method of the present invention has been largely described herein as being for the purpose of removing undue stress, balancing the ANS, and creating relaxation, other desirable mental states associated with a balanced ANS can be achieved though the methodology. These include but are not limited to brainwave states for enhanced and rejuvenating sleep, calmness, alertness, concentration, creativity, physical and emotional healing, peak performance and meditation. For example, enhanced sleep may be obtained using Delta brainwave entrainment since this is the most common brain state that chronic insomnia sufferers cannot achieve. Hence, in an embodiment rejuvenating sleep treatment session, in addition to playing the fundamental frequency of the subject 5 and, optionally, octaves thereof, a binaural beat may be played as set forth above having a frequency that is an octave of the fundamental frequency that lands within this subject's 5 Delta brainwave band to induce entrainment with the Delta brainwave. Brain states associated with calmness usually encompass various levels of Alpha, and hence treatment methods to induce calmness may employ similar techniques but instead target the Alpha brainwave. Alertness brain states involve mid-upper Beta, which are typically between 16 and 19 Hz. Concentration and Focus states involve upper Beta, which are typically between 24 to 27 Hz. Creativity states are associated with Theta brain activity and this is also where emotional healing takes place, since this is where dreaming takes place and it is in dreaming sleep that emotional issues are dealt with and healed at night during sleep. Peak performance states are associated with the borderline zone between Beta and Alpha, which although may vary from person to person is typically at around 13 Hz. Meditation has broad zones corresponding to different meditation traditions and practices. The physical body position of sitting in meditation may unlock different neural programs in the brain than entraining to the same brain frequencies while lying down.

However, entraining to the following brainwave states may induce corresponding meditative states as set forth in the following:

| Brainwave | Meditative State |
|---|---|
| Beta | Meditation-in-Action, Karma Yoga |
| Alpha | Zen/Za-Zen Meditation |
| Theta | Chakra, Kundalini, Shamanic Journey, Christian Prayer |
| Delta | white light state, timeless "void" state |
| Epsilon | Ecstatic states, pre-cognitive, psychic, out-of-body, Yogic suspended animation states |
| Gamma | Tibetan Yoga meditation "bliss" state |
| HyperGamma and Lambda | Cosmic consciousness states, union with the cosmos, great understanding states |

The desired meditative state may thus be selected and then the appropriate corresponding binaural beat frequency computed and applied to assist the subject 5 to enter into the desired state.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method, employing a real time heart rate variability (RT-HRV) monitor having a display showing the sympathetic nervous system (SNS) and the parasympathetic nervous system (PSNS) components of a subject's autonomic nervous system (ANS), for determining the fundamental frequency of the ANS of the subject and treating the subject, the method comprising:
   applying at least an external stimulus to the subject, at a first frequency;
   sweeping the frequency of the external stimulus from the first frequency to a second, different, frequency;
   monitoring, by means of the RT-HRV monitor and display, during the sweeping step the SNS component and the PSNS component of the ANS;
   determining when the subject has entered into a state of homeostasis, at which time the SNS and the PSNS are about equal as shown on the display;
   determining a frequency of the applied external stimulus that corresponds to the state of homeostasis of the subject;
   selecting as the fundamental frequency of the subject the determined frequency; and
   treating the subject for a predetermined period of time by initially applying the external stimulus at least at the fundamental frequency to achieve and maintain the subject in a state of homeostasis.

2. The method of claim 1 wherein determining when the subject has entered into a state of homeostasis comprises determining if the SNS component and the PSNS component are within at least 5% of each other.

3. The method of claim 1 wherein the frequency sweep is performed in predetermined frequency increments over a predetermined time period.

4. The method of claim 1 wherein treating the subject comprises applying one or more of vibrations at the fundamental frequency, light flickering at the fundamental frequency, and sound with a tone at the fundamental frequency.

5. The method of claim 1, and further comprising:
   continuously monitoring by means of the RT-HRV monitor the state of homeostasis of the subject; and
   micro-tuning the frequency of the external stimulus applied to the subject as necessary to maintain the subject in the state of homeostasis.

6. The method of claim 1, and further comprising applying at least one octave of the fundamental frequency to the subject during the treating stop.

7. A system for determining a fundamental frequency of a subject and applying the fundamental frequency to the subject, the system comprising:
   a monitor for monitoring the autonomic nervous system (ANS) of the subject in a continuous, real time manner, to obtain a sympathetic nervous system (SNS) component of the ANS and a parasympathetic nervous system (PSNS) component of the ANS;
   a frequency application device for applying at least an external stimulus to the subject according to an input signal; and
   a computing system coupled to the monitor and to the frequency application device, the computing system comprising at least a central processing unit (CPU) coupled to memory, the memory comprising program code executable by the CPU to cause the computing system to perform the following steps;
   generating a signal having a first frequency and outputting the signal to the frequency application device;
   sweeping the frequency applied to the subject by the frequency application device from the first frequency to a second, different, frequency;
   monitoring the SNS component and the PSNS component to determine when the subject has entered into a state of homeostasis;
   determining a value of the frequency that corresponds to the state of homeostasis of the subject;
   selecting as the fundamental frequency of the subject the determined value of the determined frequency; and
   computing at least a second frequency that is an octave of the fundamental frequency and adding the second frequency to the signal such that the signal output to the frequency application device is a combination of the fundamental frequency and the at least a second frequency.

8. The system of claim 7 wherein determining when the subject has entered into a state of homeostasis comprises determining if the SNS component and the PSNS component are within at least 5% of each other.

9. The system of claim 8 wherein determining the value of the frequency that corresponds to the state of homeostasis comprises determining the value of the frequency when the SNS component and the PSNS component are substantially equal.

10. The system of claim 7 wherein the memory further comprises information indicative of a frequency increment and a predetermined time period, and the program code causes the frequency sweep to be performed in steps according to the frequency increment in the predetermined time period.

11. The system of claim 7 wherein the frequency application device comprises one or more of a surface that vibrates at a frequency according to the input signal, a light that flickers according to the input signal and sound system that plays a tone according to the input signal.

12. The system of claim 7 wherein the monitor comprises a Real-Time Heart Rate Variability monitor.

* * * * *